United States Patent
Koh

(10) Patent No.: US 7,942,822 B1
(45) Date of Patent: May 17, 2011

(54) IMPLANTABLE MEDICAL DEVICE WITH SLEEP APNEA DETECTION CONTROL AND METHOD

(75) Inventor: Steve Koh, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 1325 days.

(21) Appl. No.: 11/461,264

(22) Filed: Jul. 31, 2006

(51) Int. Cl.
A61B 5/08 (2006.01)

(52) U.S. Cl. .......................... 600/529; 600/533; 600/538

(58) Field of Classification Search .................. 600/529, 600/538, 533
See application file for complete search history.

(56) References Cited

U.S. PATENT DOCUMENTS

| | | |
|---|---|---|
| 5,540,732 A | 7/1996 | Testerman |
| 5,895,360 A | 4/1999 | Christopherson et al. |
| 5,944,680 A | 8/1999 | Christopherson et al. |

FOREIGN PATENT DOCUMENTS

EP 0914179 B1 6/1997

*Primary Examiner* — Charles A Marmor, II
*Assistant Examiner* — Michael D'Angelo

(57) ABSTRACT

A method for use in an implantable medical device comprises the steps of monitoring respiration with an amplifier having a gain, generating a moving apneic threshold based on recent respiration cycles, accumulating differences between amplitudes of respiration cycles and the moving apnea detection threshold and comparing the accumulated differences against an apnea detection threshold to detect the onset of an episode of apnea. The method further comprises measuring respiration levels upon detecting the onset of apnea, confirming the episode of apnea based upon the respiration levels measured upon detecting the onset of apnea; and adjusting one of the gain of the amplifier and the apnea detection threshold so that the time from the detection of onset of apnea to the time of confirmation of the episode of apnea is within a predetermined time range following the detection of the onset of apnea.

20 Claims, 6 Drawing Sheets

IMPLANTABLE MEDICAL DEVICE WITH SLEEP APNEA DETECTION CONTROL AND METHOD

FIELD OF THE INVENTION

The present invention generally relates to implantable medical devices. The present invention more particularly relates to implantable cardiac devices having sleep apnea detection control.

BACKGROUND OF THE INVENTION

Implantable cardiac devices are well known in the art. They may take the form of an implantable defibrillator (ICD) to treat accelerated rhythms of the heart such as fibrillation, or an implantable pacemaker to maintain the heart rate above a prescribed limit, such as, for example, to treat a bradycardia. Implantable cardiac devices are also known which incorporate both a pacemaker and a defibrillator.

The devices are generally implanted in an upper portion of the left-side of the chest beneath the skin of a patient within what is known as a subcutaneous pocket. The implantable devices generally function in association with one or more electrode-carrying leads which are implanted within the heart. The electrodes are positioned within the heart, for making electrical contact with their designated heart chamber. Conductors within the leads couple the electrodes to the device to enable the device to deliver the desired therapy.

Pacemakers deliver pacing pulses to the heart to cause the stimulated heart chamber to contract when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Pacemakers are described as single-chamber or dual-chamber systems. A single-chamber system stimulates and senses in one chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode.

For defibrillation, one lead may include at least one defibrillation electrode arranged to be positioned in the right ventricle. When fibrillation is detected, a pulse generator delivers a defibrillating shock from the defibrillation electrode in the right ventricle to the device conductive housing to terminate the arrhythmia. Alternatively, a further defibrillation electrode may be positioned in the right atrium or superior vena cava and electrically connected to the right ventricular defibrillation electrode. In this arrangement, the defibrillating shock is delivered from the parallel connected defibrillation electrodes to the conductive housing.

Sleep apnea is a serious, potentially life-threatening condition characterized by brief interruptions of breathing during sleep. In a given night, the number of involuntary pauses in breathing (apneic events) may be as high as twenty to sixty or more per hour. During sleep apnea, blood oxygen saturation levels are reduced. These reduced blood oxygen saturation levels can be especially serious for patients with congestive heart failure (CHF).

As is known, CHF disease state may be evaluated through impedance measurements utilizing electrodes implanted in the heart. Such measurements may be carried out by applying a current between a pair of the electrodes and measuring the voltage between those electrodes or another pair of electrodes. Hence, an implanted cardiac stimulation device is well suited for such an application. Sleep apnea may also be monitored in this manner.

Implantable cardiac devices are also well suited for providing sleep apnea therapy. One such therapy is phrenic nerve stimulation (PNS). Here, stimulation pulses from the device's pulse generator are applied to phrenic nerves associated with the diaphragm or to diaphragm muscle itself. Both of these forms of stimulation therapy are included herein as PNS.

Another form of therapy which an implantable cardiac device is well suited to provide is overdrive pacing. Here, stimulation pulses are provided to the heart to increase the cardiac rate and cardiac output. The stimulation pulses may be in accordance with a pacing modality referred to as DAO pacing where both the atrial and ventricles are paced. The atrial pacing rate is above a base rate and a ventricular pacing pulse is provided an escape interval after each atrial pacing pulse. DAO pacing is considered effective at preventing central sleep apnea because the higher cardiac rate will increase cardiac output which in turn will decrease the delay in the respiratory control loop.

Sleep apnea may be defined as the lack of respiratory function for a period of time such as, for example, ten seconds. Unfortunately, not long after that lack of respiratory function, blood saturation levels may already be dangerously reduced. Hence, it is most advantageous to confirm apnea and provide therapy as soon as possible after the apnea episode may be confirmed. Otherwise, harm to the patient may result. Hence, it would be most advantageous to be able to detect sleep apnea early to enable an early sleep apnea confirmation and therapy.

Such early sleep apnea detection may be carried out as described, for example, in U.S. patent application Ser. No. 10/883,857, filed on Jun. 30, 2004 for SYSTEM AND METHOD FOR REAL-TIME APNEA/HYPOPNEA DETECTION USING AN IMPLANTABLE MEDICAL SYSTEM, which application is hereby incorporated herein by reference in its entirety. This allows the sleep apnea to be detected before the condition has persisted too long to cause harm without intervention. Therapy may then be applied early enough to preclude serious de-saturation.

Impedance monitoring to measure respiration is generally carried out with a variable gain amplifier. In the detection of apnea, as described in the aforementioned referenced application, the impedance signal is compared to a running average or threshold. The difference between the two is an error that is accumulated. When the accumulated error equals a detection threshold, detection of apnea is declared. How soon this occurs before the apnea is actually confirmed is largely dependent upon the gain of the variable gain amplifier. If the gain is too high, the error accumulates too fast resulting in too short a time until confirmation and possible confirmation error. If the gain is too low, the error can accumulate too slowly to unduly delay apnea detection until well after apnea onset and may even preclude apnea detection all together. Hence, the present invention addresses these issues concerning apnea detection control to assure that the time from apnea detection to apnea confirmation is neither too long nor too short.

SUMMARY

What is described herein is a method for use in an implantable medical device comprising monitoring respiration with a variable gain amplifier, generating a moving apneic threshold based on recent respiration cycles, accumulating differences between amplitudes of respiration cycles and the moving apnea detection threshold, detecting the onset of an episode of apnea based upon the accumulated differences, measuring respiration levels upon detecting the onset of apnea, confirming the episode of apnea based upon the respiration levels measured upon detecting the onset of apnea, and adjusting the gain of the variable gain amplifier so that the time from the detection of onset of apnea to the time of confirmation of the episode of apnea is within a predetermined time range.

The predetermined time range may be between ten seconds and twenty seconds. The step of detecting the onset of an episode of apnea based upon the accumulated differences may be performed by comparing the accumulated differences against a fixed apnea detection threshold.

The step of measuring respiration levels may be performed by making respiration measurements at preset time intervals upon and after detecting the onset of apnea. The step of confirming the episode of apnea may be based upon making a set number of consecutive respiration measurements of apnea respiration levels within the predetermined time range. The preset time intervals may be on the order of five seconds. The set number may be at least three. The time range may be on the order of ten seconds. The method may further include the step of delivering apnea therapy upon confirmation of the onset of an episode of apnea.

In another embodiment, a method for use on an implantable medical device comprises the steps of monitoring respiration with an amplifier having a gain, generating a moving apneic threshold based on recent respiration cycles, accumulating differences between amplitudes of respiration cycles and the moving apnea detection threshold, detecting the onset of an episode of apnea based upon the accumulated differences and an apnea detection threshold, measuring respiration levels upon detecting the onset of apnea, confirming the episode of apnea based upon the respiration levels measured upon detecting the onset of apnea, and adjusting one of the gain of the amplifier and the apnea detection threshold so that the time from the detection of onset of apnea to the time of confirmation of the episode of apnea is within a predetermined time range.

In another embodiment, an implantable medical device comprises a respiration monitor including an amplifier having a gain, an apnea detector that generates a moving apneic threshold based on recent respiration cycles, accumulates differences between amplitudes of respiration cycles and the moving apnea detection threshold, and compares the accumulated differences against an apnea detection threshold to detect the onset of an episode of apnea. The respiration monitor measures respiration levels upon the detection of the onset of apnea. The device further comprises an apnea confirming circuit that confirms the episode of apnea based upon the respiration levels measured upon the detection of the onset of apnea and a control circuit that adjusts one of the gain of the amplifier and the apnea detection threshold so that the time from the detection of onset of apnea to the time of confirmation of the episode of apnea is within a predetermined time range.

In another embodiment, a method for use in an implantable medical device comprises the steps of monitoring respiration with an amplifier having a fixed gain, generating a moving apneic threshold based on recent respiration cycles, accumulating differences between amplitudes of respiration cycles and the moving apnea detection threshold, and detecting the onset of an episode of apnea based upon the accumulated differences and an apnea detection threshold. The method further comprises measuring respiration levels upon detecting the onset of apnea, confirming the episode of apnea based upon the respiration levels measured upon detecting the onset of apnea, and adjusting the apnea detection threshold so that the time from the detection of onset of apnea to the time of confirmation of the episode of apnea is within a predetermined time range.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
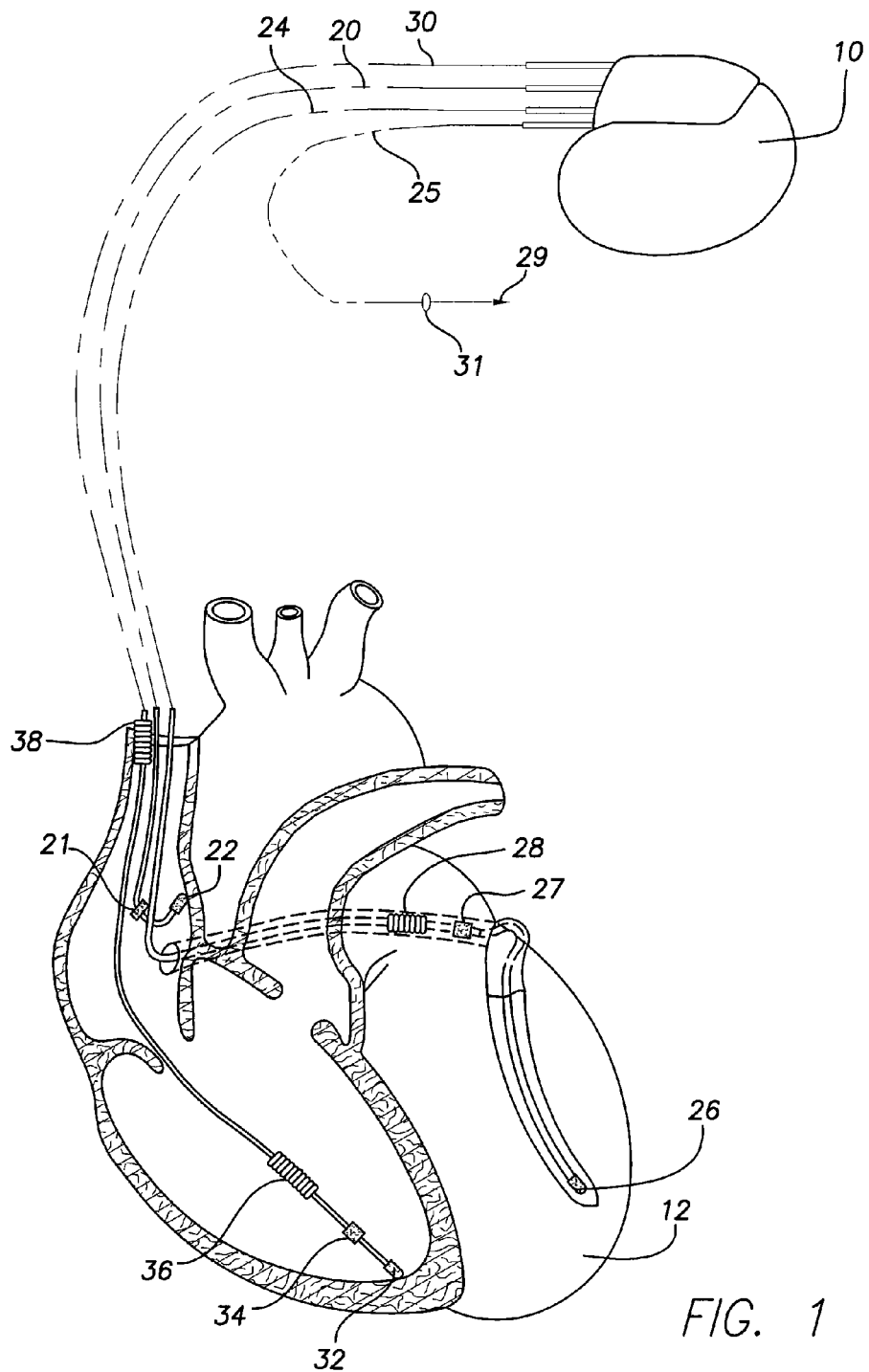
FIG. 1 is a simplified diagram illustrating an implantable cardiac stimulation device embodying the present invention.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial ring electrode 21 and an atrial tip electrode 22, which are typically implanted in the patient's right atrial appendage. The electrodes 21 and 22 form a bipolar electrode pair useful for right atrial pacing and near field targeted atrial activity sensing.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

The device 10 includes a still further lead 25. The lead 25 includes a distal electrode 29 and a proximal electrode 31. The electrodes 31 and 29 may be coupled to the nervous system of the patient for applying phrenic nerve stimulation (PNS) apnea therapy when detection of apnea is confirmed as described hereinafter.

Figure 2:
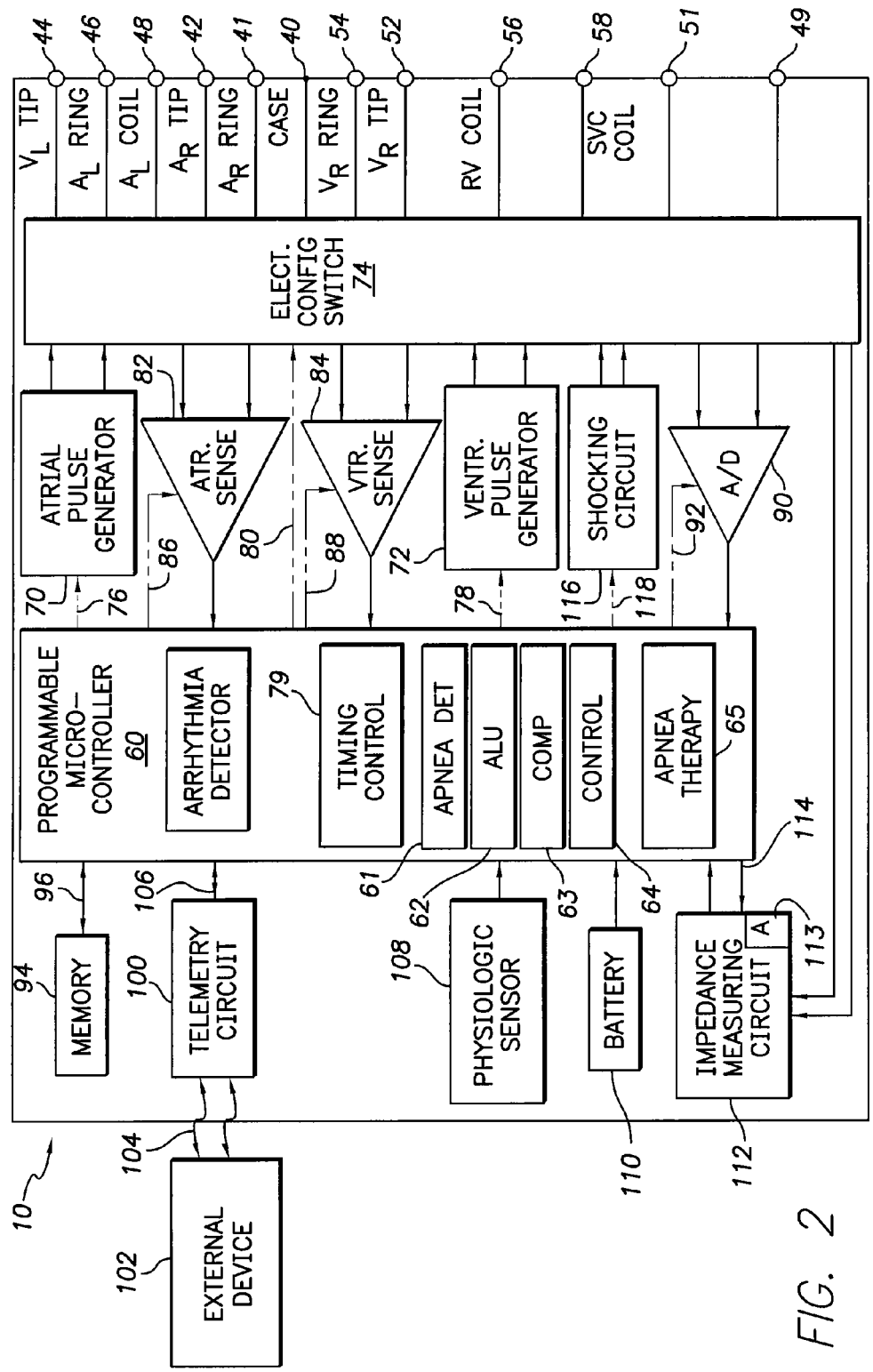
FIG. 2 is a functional block diagram of the implantable cardiac stimulation device of FIG. 1 according to one embodiment of the invention.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 41, 42, 44, 46, 47, 48, 49, 51, 52, 54, 56, and 58 (shown schematically and, for convenience, the names of the electrodes to which they are connected are shown next to the terminals). As such, to achieve right atrial sensing and pacing, the connector includes at least a right atrial ring terminal ($A_R$ RING) 41 and a right atrial tip terminal ($A_R$ TIP) 42 adapted for connection to the atrial ring and tip electrodes 21 and 22, respectively.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively. Lastly, to achieve vagal or phrenic nerve stimulation, the electrode 31 may be coupled to terminal 51 and the electrode 29 may be coupled to terminal 49.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74 and PNS pulse for delivery by the PNS lead 25. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of timing periods, as, for example, refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may employ lithium/silver vanadium oxide batteries.

As further shown in FIG. 2, and according to this embodiment, the device 10 includes an impedance monitor or measuring circuit 112 comprising a variable gain amplifier 113. The measuring circuit 112 is controlled by the microcontroller 60 via a control signal 114 which, according to this embodiment, controls or varies the gain of the variable gain amplifier 113. As is known, the impedance measuring monitor 112 may be used for lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used. For example, according to this embodiment, the case 40 may serve as one impedance monitoring electrode, and one of electrodes 32, 34, or 36 may be employed as the second impedance monitoring electrode.

More specifically, to measure impedance for detecting sleep apnea, the impedance monitor 112 applies a current between at least two electrodes, as for example among those previously mentioned, and selected by switch 74. As the current is applied, the induced voltage across those electrodes or another electrode pair is sensed. A signal may then be generated representing the respiration of the patient.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
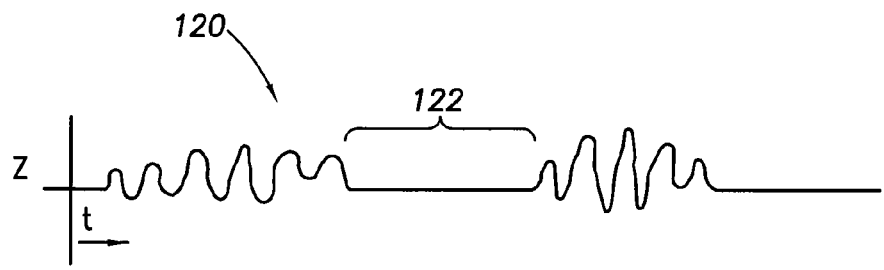
FIG. 3 is a graphical representation of a respiration signal according to an embodiment of the invention.

As may also be seen in FIG. 2, the device 10 further includes an apnea detector 61, an apnea detector control 64, and an apnea therapy control 65. The apnea detector 61 includes an arithmetic logic unit (ALU) 62 and a comparator circuit 63. The apnea detector 61 utilizes the respiration signal provided by the impedance monitor 112 to detect the onset of apnea. More particularly, and as described in the previously referenced application Ser. No. 10/883,857, and as shown in FIG. 3, a varying impedance signal representing varying respiration 120 has peak to peak amplitudes related to the monitored impedance and the gain of the amplifier 113. The cyclical nature of the signal 120 is representative of breathing by the patient. It may be noticed that there is a lack of activity in the signal 120 during a period 122. This period 122 is an episode of apnea.

Figure 4:
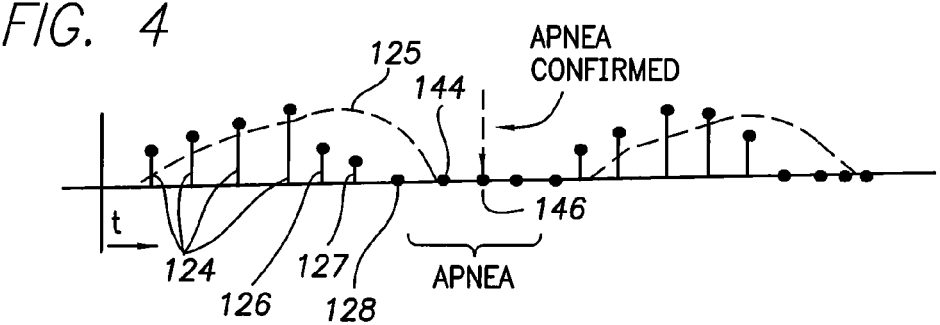
FIG. 4 is a graphical representation of cyclical-by-cycle measurements of the respiration signal of FIG. 3, and a running average of the measurements.

FIG. 4 shows that for each cycle in the signal 120, the apnea detector 61 takes a peak to valley measurement 124. From these measurements, the apnea detector 61 uses the ALU 62 to determine a varying threshold 125 which is a running average of, for example, the last three measurements 124 of signal 120.

Figure 5:
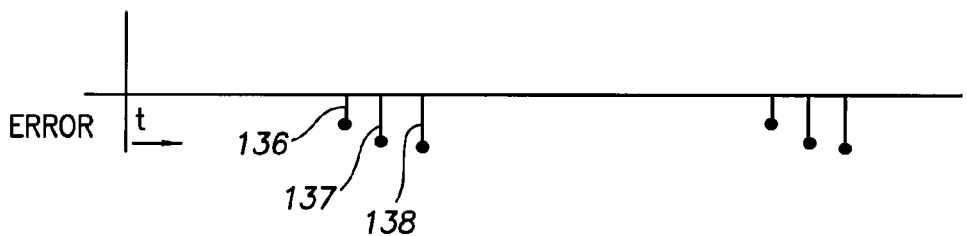
FIG. 5 is a graphical representation of differences between the respiration signal measurements and running average of the measurements.
Figure 6:
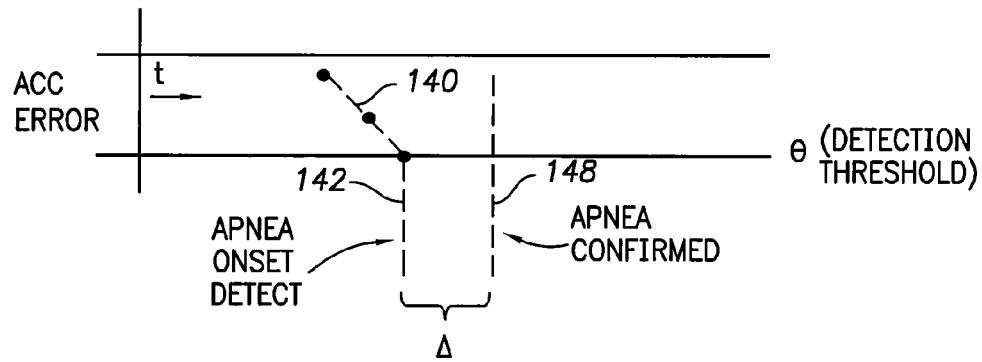
FIG. 6 is a graphical representation of accumulated differences between the respiration signal measurements and running average of the measurements and the time (delta) from apnea detection with a fixed detection threshold (theta) to apnea confirmation.

The signal measurements 124 are compared by the comparator 63 to the varying threshold 125. When a signal measurement, such as measurements 126, 127 and 128 is less than the running average 125, the difference between these measurements and the running average is determined by the ALU 62. FIG. 5 shows these differences as errors 136, 137 and 138 which correspond to measurements 126, 127, and 128 respectively. As the errors are determined, the ALU accumulates them as shown in FIG. 6. The accumulated error follows a dashed line 140. When the accumulated error equals a fixed threshold θ (theta), detection of apnea onset is declared. This occurs at time 142 in FIG. 6.

After the onset of apnea is declared, the signal 120 continues to be measured. However, since there is no respiration and hence no cyclical variation in signal 120, the measurements are taken at spaced part times. In this embodiment, the measurements are taken every 5 seconds. Also for this embodiment, apnea is defined as the taking of three consecutive measurements having at apnea level (zero) respiration levels. As shown in FIG. 4, these three consecutive measurements are measurements 128, 144, and 146. Upon the last (third) such measurement, measurement 146, the detection of apnea is confirmed. This occurs at time 148 shown in FIG. 6. At this point in time, the therapy control can initiate apnea therapy such as DAO pacing or PNS.

As may thus be noted in FIG. 6, there is a time period Δ (delta) which extends from the time of detection 142 until the time of confirmation 148. As previously explained, it is desirable to maintain delta within a certain range to make sure that apnea therapy is provided in a timely manner. For example, it may be desirable to maintain delta between about 8 and 16 seconds. Since the measurements 124 are taken every five seconds in this embodiment, delta in this case is ten seconds, well within the permitted range for delta.

Maintenance of delta within the permitted range may be accomplished by varying the gain of the amplifier 113. For example, if the gain is increased, the error will accumulate much faster, thus increasing delta. If the error is permitted to accumulate too fast, improper detection with false positives may result. Conversely, if the gain is decreased, the error will accumulate more slowly, thus shortening delta. In fact, if the gain becomes too low, the error may accumulate so slowly that apnea would not even be detected (false negatives).

Figure 7:
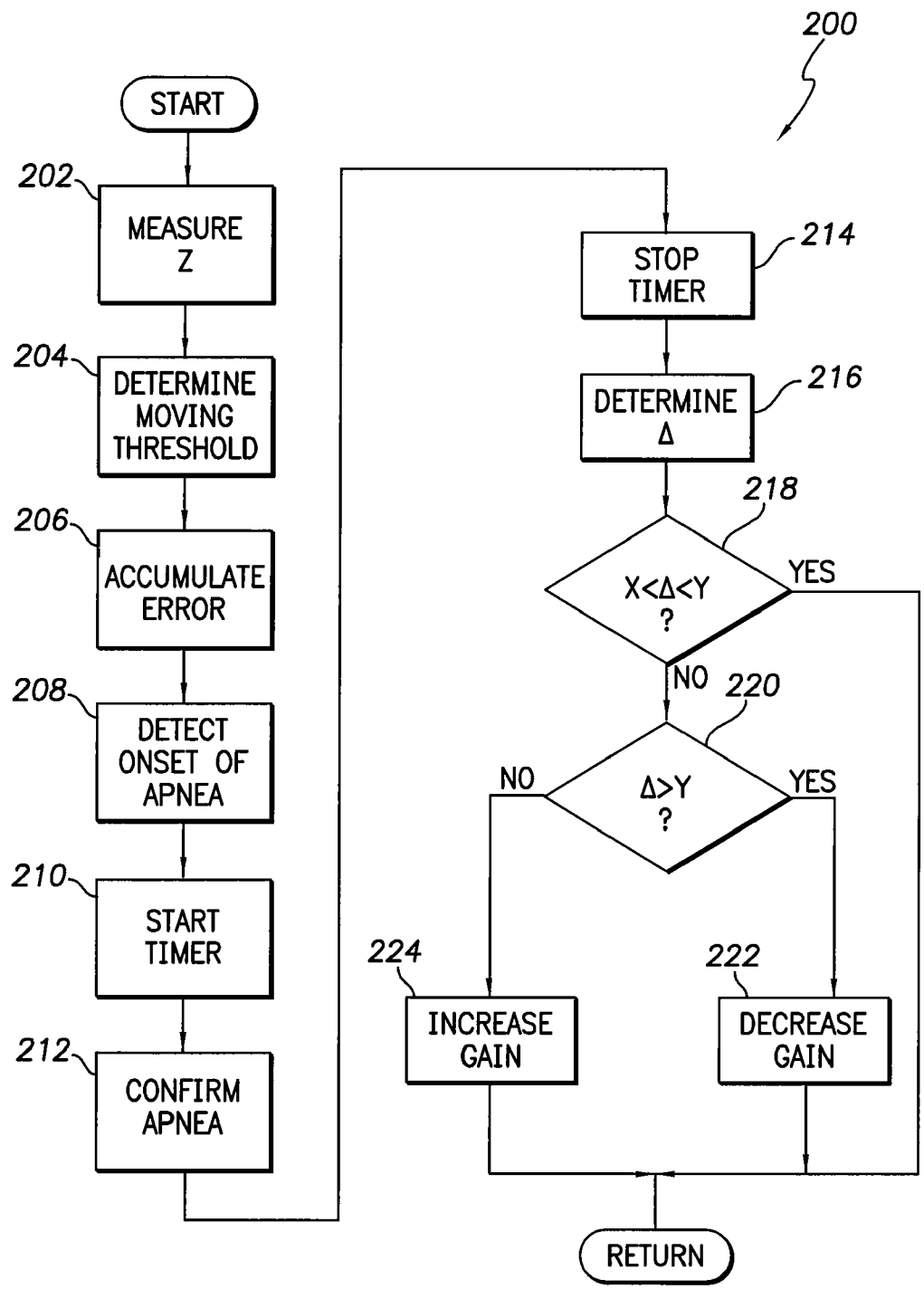
FIG. 7 is a flow diagram describing an overview of one embodiment of the invention.

Referring now to FIG. 7, it is a flow chart describing the overview of the operation and novel features implemented in one embodiment of the device 10 in accordance with the present invention. In this flow chart, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

Referring now to FIG. 7, the process 200 shown initiates with activity block 202. Here, the impedance signal 120 is measured to measure the respiration. Next, in activity block 204, the next point in the moving threshold 125 is determined. The process then advances to activity block 206 where the error is accumulated. Next, in activity block 208, the accumulated error exceeds the fixed apnea detection threshold theta to enable apnea detection to be declared.

The process then advances to activity block 210 wherein a timer is started to time delta. The timer may be, for example, the timing control 79 of FIG. 2. Thereafter, in accordance with activity block 212, the apnea detection is confirmed. The timer is then stopped in activity block 214. At this time, the therapy control 65 may initiate apnea therapy.

The process now advances to activity block 216 wherein delta, the time from apnea detection to the time of apnea confirmation is determined from the timing clock. Next, in decision block 218, it is determined if delta is less than an upper range limit Y and greater than a lower range limit X. If the outcome is in the affirmative, delta is within range and the process returns. However, if the outcome is in the negative, the process advances to decision block 220 where it is determined if delta is greater than the upper range limit Y. If it is, Delta is too long. As a result, the process then advances to activity block 222 where the gain of amplifier 113 is decreased. This will cause delta to decrease upon the next apnea detection and confirmation.

If the outcome of decision block 220 is negative, it will be known the delta must be less than the lower range limit for delta. Accordingly, in activity block to follow, the gain of the amplifier 113 is increased to increase delta. As may be appreciated, by repeating the foregoing, delta may be maintained within the permitted range.

While this embodiment has been directed to varying the gain of amplifier 113 with a fixed detection threshold theta, those skilled in the art will appreciate that the gain may be fixed and the detection threshold (theta) varied. In this case, as may be discerned from FIG. 6, decreasing the threshold theta will decrease delta and increasing the threshold theta will increase delta.

This may be implemented in accordance with the flow chart of FIG. 7 with only slight modification. To that end, if the result of decision block 218 is negative and thereafter the result of decision block 220 is affirmative, then activity block 222 would call for a reduction of the threshold theta. If instead, the result of decision block 220 is affirmative, then activity block 224 would call for an increase in the threshold theta. Following either activity block 222 or activity block 224, the process returns for the next interaction, if necessary.

Figure 8:
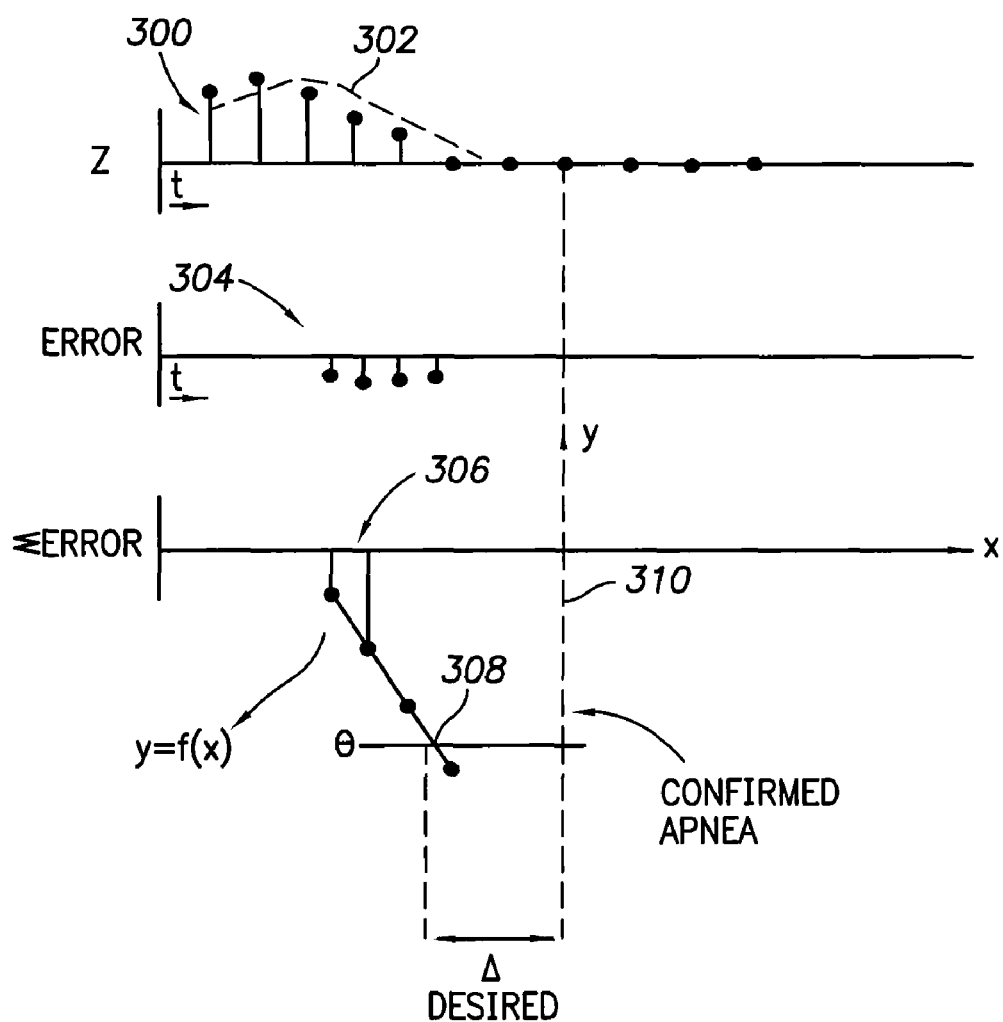
FIG. 8 is a graphical representation of accumulated differences between respiration signal measurements and a running average of the measurements and the time (delta) from apnea detection to apnea confirmation with a fixed gain and variable detection threshold (theta)

To further illustrate this alternative embodiment, reference may be had to FIG. 8. FIG. 8 illustrates a fixed gain with variable threshold embodiment while FIG. 6 illustrates a variable gain with fixed threshold embodiment. Here, are represented, cycle-by-cycle measurements 300 of a respiration signal and a running average 302 of those measurements, the differences or error 304 between the respiration signal measurements 300 and the running average 302, and the accumulated error 306 of the differences 304.

The accumulated error may define a function: y=f(x). When f(x) equals the detection threshold θ, as at 308, apnea detection is declared. Confirmation of the apnea detection occurs at 310 when, as previously described, three consecutive respiration measurements are zero. The time from apnea detection 308 to apnea confirmation 310 is delta (Δ).

Figure 9:
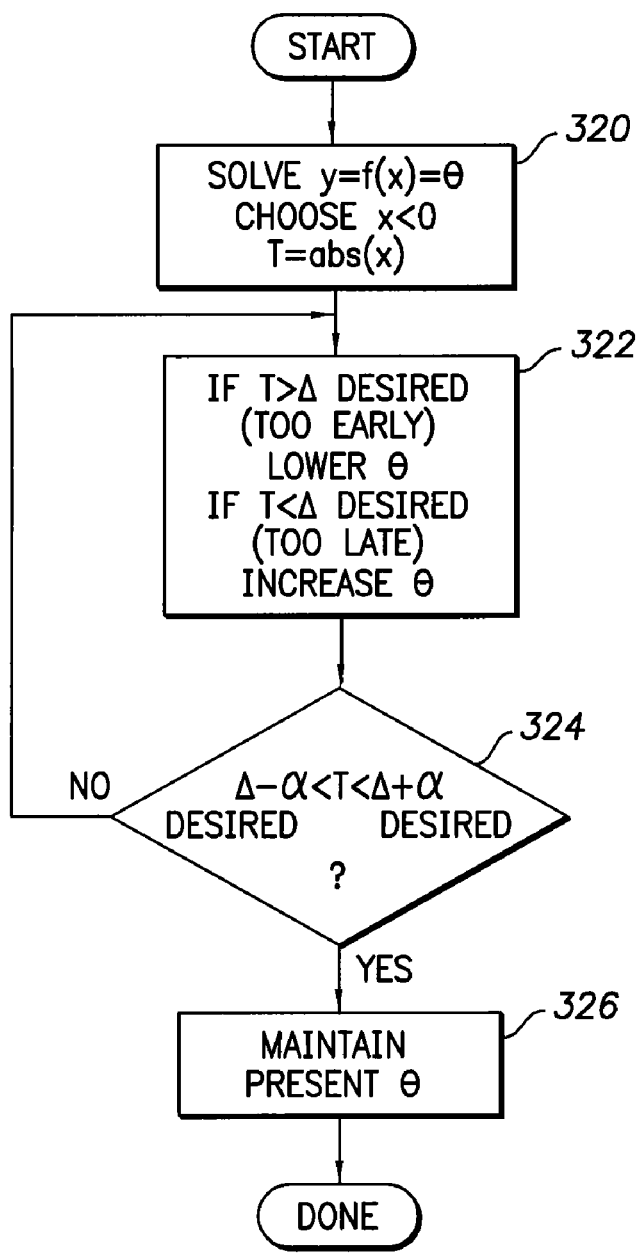
FIG. 9 is a flow diagram illustrating a manner in which the apnea detection threshold (θ) may be adjusted to provide a delta within a desired range.

FIG. 9 is a flow chart showing a manner in which the apnea detection threshold θ may be varied with a fixed gain to obtain a delta within desired limits. The flow diagram initiates with activity block 320 wherein the function, f(x)=θ, is solved. For this, the value of x is chosen to be less than zero and T, used in the next activity block 322 is taken as the absolute value of x.

Next, in activity block 322, if T is less than the desired Δ (too late), the detection threshold θ is increased.

The process then proceeds to decision block 324. Here it is determined if T is within desired limits of Δ. Those limits may be, for example, the desired Δ plus or minus a set interval α, which may be a few seconds. If T is outside of the desired Δ limits, the process returns to activity block 322. If T is within the desired limits of Δ, the current value of θ is maintained in accordance with activity block 326 and the process completes.

While the invention has been described by means of specific embodiments and applications thereof, it is understood that numerous modifications and variations may be made thereto by those skilled in the art without departing from the spirit and scope of the invention. It is therefore to be understood that within the scope of the claims, the invention may be practiced otherwise than as specifically described herein.

What is claimed is:

1. A method for use in an implantable medical device, the method comprising:
   monitoring respiration with a variable gain amplifier;
   generating a moving apneic threshold based on recent respiration cycles;
   accumulating differences between amplitudes of respiration cycles and the moving apnea detection threshold;
   detecting the onset of an episode of apnea based upon the accumulated differences;
   measuring respiration levels upon detecting the onset of apnea;
   confirming the episode of apnea based upon the respiration levels measured upon detecting the onset of apnea; and
   adjusting the gain of the variable gain amplifier so that the time from the detection of onset of apnea to the time of confirmation of the episode of apnea is within a predetermined time range.

2. The method of claim 1, wherein the predetermined time range is between ten seconds and twenty seconds.

3. The method of claim 1, wherein detecting the onset of an episode of apnea based upon the accumulated differences is performed by comparing the accumulated differences against a fixed apnea detection threshold.

4. The method of claim 1, wherein measuring respiration levels is performed by making respiration measurements at preset time intervals upon and after detecting the onset of apnea.

5. The method of claim 4, wherein confirming the episode of apnea is based upon making a set number of consecutive respiration measurements of apnea respiration levels within the predetermined time range.

6. The method of claim 1, further comprising delivering apnea therapy upon confirmation of the onset of an episode of apnea.

7. A method for use in an implantable medical device, the method comprising:
   monitoring respiration with an amplifier having a gain;
   generating a moving apneic threshold based on recent respiration cycles;
   accumulating differences between amplitudes of respiration cycles and the moving apnea detection threshold;
   detecting the onset of an episode of apnea based upon the accumulated differences and an apnea detection threshold;
   measuring respiration levels upon detecting the onset of apnea;
   confirming the episode of apnea based upon the respiration levels measured upon detecting the onset of apnea; and
   adjusting one of the gain of the amplifier and the apnea detection threshold so that the time from the detection of onset of apnea to the time of confirmation of the episode of apnea is within a predetermined time range.

8. The method of claim 7, further comprising delivering apnea therapy upon confirmation of the onset of an episode of apnea.

9. The method of claim 7, wherein the predetermined time range is between ten seconds and twenty seconds.

10. The method of claim 7, wherein adjusting comprises adjusting the gain of the amplifier and wherein detecting the onset of an episode of apnea comprises comparing the accumulated differences against a fixed apnea detection threshold.

11. The method of claim 7 wherein measuring respiration levels is performed by making respiration measurements at preset time intervals upon and after detecting the onset of apnea.

12. An implantable medical device, comprising:
   a respiration monitor including an amplifier having a gain;
   an apnea detector that generates a moving apneic threshold based on recent respiration cycles, accumulates differences between amplitudes of respiration cycles and the moving apnea detection threshold, and compares the accumulated differences against an apnea detection threshold to detect the onset of an episode of apnea; the respiration monitor measuring respiration levels upon the detection of the onset of apnea,
   an apnea confirming circuit that confirms the episode of apnea based upon the respiration levels measured upon the detection of the onset of apnea; and a control circuit that adjusts one of the gain of the amplifier and the apnea detection threshold so that the time from the detection of onset of apnea to the time of confirmation of the episode of apnea is within a predetermined time range.

13. The device of claim 12, further comprising a therapy circuit that delivers apnea therapy upon confirmation of the onset of an episode of apnea.

14. The device of claim 12, wherein the predetermined time range is between ten seconds and twenty seconds.

15. The device of claim 12, wherein the control circuit adjusts the gain of the amplifier and wherein the detector detects the onset of an episode of apnea by comparing the accumulated differences against a fixed apnea detection threshold.

16. The device of claim 12 wherein the respiration monitor makes respiration measurements at preset time intervals upon and after detection of the onset of apnea.

17. The device of claim 16, wherein the apnea confirming circuit confirms the episode of apnea based upon the respiration monitor making a set number of consecutive respiration measurements of apnea respiration levels within the predetermined time range.

18. The device of claim 17, wherein the preset time intervals are on the order of five seconds.

19. The device of claim 17, wherein the set number is at least three.

20. The device of claim 17, wherein the time range is on the order of ten seconds.

* * * * *